US006491947B2

(12) United States Patent
Moore et al.

(10) Patent No.: US 6,491,947 B2
(45) Date of Patent: Dec. 10, 2002

(54) EXPANDED PERBORATE SALT, USE, AND METHOD OF PRODUCTION

(75) Inventors: Ryan Giffin Moore, Lilburn, GA (US); Hilton G. Dawson, Canton, GA (US); Richard A. DeSenna, Duluth, GA (US); Kenneth Scott Wiley, Oakwood, GA (US)

(73) Assignee: ChemLink Laboratories, LLC, Kennesaw, GA (US)

( * ) Notice: Subject to any disclaimer, the term of this patent is extended or adjusted under 35 U.S.C. 154(b) by 0 days.

(21) Appl. No.: 09/932,766

(22) Filed: Aug. 17, 2001

(65) Prior Publication Data

US 2002/0090343 A1 Jul. 11, 2002

Related U.S. Application Data

(63) Continuation-in-part of application No. 09/858,020, filed on May 15, 2001.
(60) Provisional application No. 60/245,540, filed on Nov. 3, 2000.

(51) Int. Cl.$^7$ ............................. A61K 9/14; A61K 9/20
(52) U.S. Cl. ..................... 424/466; 424/76.1; 424/405; 424/489
(58) Field of Search ................................ 424/401, 405, 424/464, 466, 489, 76.1

(56) References Cited

U.S. PATENT DOCUMENTS

| 3,661,510 A | * | 5/1972 | Winkley ........................ 23/60 |
| 4,211,759 A | * | 7/1980 | Mollard ....................... 423/281 |
| 6,071,539 A | | 6/2000 | Robinson et al. ........... 424/466 |
| 6,096,703 A | | 8/2000 | Hall ............................ 510/411 |

FOREIGN PATENT DOCUMENTS

| EP | 0 102 418 A1 | 8/1982 | ............ A61K/7/30 |
| EP | 0 102 419 A1 | 8/1982 | ............ A61K/7/30 |
| EP | 0 102 419 B1 | 2/1986 | ............ A61K/7/30 |

(List continued on next page.)

OTHER PUBLICATIONS

Peroxygens from Solvay Interox, Copyright 2000, pp. 1–12, www.solvayinterox.com/pcs.htm.

(List continued on next page.)

*Primary Examiner*—James M. Spear
(74) *Attorney, Agent, or Firm*—James W. Kayden; Thomas, Kayden, Horstemeyer & Risley, LLP

(57) ABSTRACT

An effervescent compound is disclosed which includes a liquid ingredient, an effervescent system and optionally a solvent. The solvent may be either hydrophobic or hydrophilic, and may have low solubility with effervescent ingredients. The solvent may include an alcohol, a glycol or a glycol ether, for example, but not limited to, 2-butoxyethanol. The effervescent system used in the effervescent compound may be, for example, but not limited to, an expanded perborate salt, anhydrous, or a mixture of an expanded perborate salt, anhydrous, and oxoborate or an acid and one or more of sodium bicarbonate, sodium carbonate, potassium bicarbonate and potassium carbonate. The effervescent compound may further include any one, or all, or any combination of the following ingredients: surfactants, bleaching compositions, anti-redeposition agents, binders, lubricants, colors, fragrances, corrosion inhibitors, disinfectants, pesticides, fertilizers and/or optical brighteners. Further disclosed is a method of producing the expanded perborate salt, anhydrous. Also disclosed is a method for making an effervescent compound, including the steps of providing a solvent, providing an effervescent system in powder form, and mixing the solvent with the effervescent system, thereby producing a free-flowing effervescent compound. The method disclosed may also include the steps of compressing the effervescent compound, and then forming either granules or a tablet.

48 Claims, 1 Drawing Sheet

FOREIGN PATENT DOCUMENTS

| | | | | |
|---|---|---|---|---|
| EP | 0 217 454 A2 | 9/1986 | | C01B/7/30 |
| EP | 0 102 418 B1 | 4/1987 | | A61K/7/30 |
| EP | 0 217 454 | 4/1987 | | 15/12 |
| EP | 0 253 772 A2 | 7/1987 | | A61K/7/30 |
| EP | 0 866 118 A1 | 3/1988 | | C11D/17/06 |
| EP | 0 444 858 A1 | 2/1991 | | C11D/1/68 |
| EP | 0 217 454 B1 | 3/1992 | | C01B/15/12 |
| EP | 2 331 994 | 2/1997 | | C11D/17/00 |
| EP | 0 913 515 A1 | 10/1997 | | D06L/3/02 |
| EP | 0 922 756 A1 | 1/1998 | | C11D/17/00 |
| EP | 0 866 118 A2 | 3/1998 | | C11D/17/06 |
| FR | 2 417 470 | 2/1978 | | C01B/15/12 |
| WO | WO 98/19511 A2 | 11/1997 | | C07D/307/87 |
| WO | WO 99/58444 A2 | 5/1999 | | C01B/15/00 |
| WO | WO 99/58632 A1 | 5/1999 | | C11D/3/00 |

OTHER PUBLICATIONS

Technical Data Sheet Sodium Perorate Monohydrate ($NaBo_3$ $H_2O$,) Copyright 2000, pp. 1–3, www.solvay-interox.com/pdfs/techdata/MM–095. pdf.

Material Safety Data Sheet Sodium Perborate Monohydrate, Copyright 2000, pp. 1–11, www.solvayinterox.com/pdf-s.msds/ZIMPBS00105.pdf.

* cited by examiner

EXPANDED PERBORATE SALT, USE, AND METHOD OF PRODUCTION

CLAIM OF PRIORITY AND CROSS-REFERENCE TO RELATED APPLICATIONS

This application is related to and claims priority to copending U.S. provisional patent application entitled "Expanded Perborate And Method Of Production" filed on Nov. 3, 2000 and accorded serial No. 60/245,540, which is entirely incorporated herein by reference, and is a continuation-in-part of U.S. patent application entitled "Expanded Perborate Salt, Use, and Method of Production," filed on May 15, 2001 and accorded Ser. No. 09/858,020, which is entirely incorporated herein by reference.

TECHNICAL FIELD

The present invention is generally related to effervescent products, and, more particularly, is related to effervescent products including perborate salts, and to a method for producing same.

BACKGROUND OF THE INVENTION

One major limitation in effervescent cleaning, disinfecting, or other products was the amount and type of liquid and active ingredients that could be incorporated into effervescent formulations. Generally, less than 25% by weight of an effervescent formulation in the form of a tablet or effervescent granules was available for active ingredients. Typically, surfactants, e.g., anionic, nonionic, cationic and amphoteric surfactants, could be used at no more than 5% of the effervescent formulas because these ingredients reduced the storage stability of carbonate-based effervescent products, made conventional granulation or tableting difficult or impossible, and dramatically increased the dissolution time of the resulting products. If greater than 5% by weight surfactants was used, then it usually became necessary to use disintegrants to enable dissolution of the composition.

Generally, solvents were incompatible with effervescent products. They were either very hydrophobic and were incompatible with aqueous systems, or were sufficiently hydrophilic to initiate the effervescent reaction, thus making the product unstable. Many surfactants were available only as liquids containing water or alcohol and could not be employed at any useful level in effervescent formulas. Previously, solvents were primarily used in effervescent tablet production for wet granulation and were evaporated in order to produce a finished tablet.

As noted previously, in typical effervescent tablets, less than 25% by weight of the tablet was usually available for ingredients other than the effervescent system. For example, although up to 75% by weight of the tablet weight could be a binder, only about 10% to 25% was typically used. The effervescent system typically accounted for up to 50% of the tablet. It should be noted that the more of the effervescent system that was used, the quicker the tablet dissolved, but less of the tablet was available for other desired ingredients. Lubricants, which help in tablet production, comprised up to approximately 10% by weight of the conventional tablet. Fragrance and color made approximately 2% of the tablet. It was found in conventional tablets that higher levels of fragrance adversely affected tablet stability, dissolution, hardness and tablet production.

One solution has been to replace the typical carbonate-based system with anhydrous perborate salt. The use of sodium perborate anhydrous in non-aqueous liquid-built detergent compositions is disclosed in Great Britain Patent Number GB-A-No. 1,205,711 (the '711 patent). The '711 patent, though, gives no further details are given of what is exactly meant by sodium perborate, anhydrous, and does not address improved dispersibility of the detergent in the wash water by addition of sodium perborate anhydrous.

Anhydrous perborate has also been noted as a potential effervescent system, which upon contact with water provides oxygen gas. For example, U.S. Pat. No. 4,772,412 (the '412 patent), issued to Green, et al., discloses a process for making an anhydrous perborate that can be used in non-aqueous liquid detergents.

Effervescent compounds have been developed that include anhydrous perborate salts for the purpose of improving the dispensing or dissolution of detergent compositions into the washing water or for improvement of the delivery of the detergent actives of the composition to the wash or for improved sudsing. See, for example, Patent Cooperation Treaty Application Number US99/10008, International Publication Number WO 99/58444 (the 10008 application) and Patent Cooperation Treaty Application Number US99/10007, International Publication Number WO 99/58632 (the 10007 application). However, the 10008 application provides that the anhydrous perborate salt be intimately mixed with a diluent, which could be a process that would add time and cost to the manufacture of the end product detergent. Further, the mixture of the anhydrous perborate salt and diluent is either dehydrated, or the solvent of the non-aqueous diluent is dried, further adding to the time and cost of producing the end product detergent. Additionally, depending on the conditions of the dehydration of the hydrated perborate salt, or the drying process of the diluent, certain amounts of hydrated perborate salt may be present in the product of the 10008 application, which limits the product to uses where bleaching action is acceptable.

In addition to the diluent that may be mixed with the anhydrous perborate salt, the 10007 Application provides that the anhydrous perborate salt be coated with a coating material in order to improve its stability. While this relieves the need for incorporation of high levels of perborate, monohydrate, it adds a further step to the production of the detergent compound, thereby increasing time and cost of the manufacture, as well as the weight and size of the end product detergent particles.

One conventional form of sodium perborate, anhydrous (oxoborate) is manufactured by and commercially available from Degussa-Hüills AG in Frankfurt, Germany. It can be produced as described in European Patent Number EU0053859, generally by application of heat to a hydrated perborate salt, and under vacuum so as to draw off immediately any vapor released upon the application of heat. The commercially available oxoborate effervesces, but is difficult to use in tablets without the addition of additives. See U.S. Pat. Nos. 4,409,118 and 4,857,224. When loaded with solvents or liquid ingredients, the oxoborate begins to clump when the solvents or liquid ingredients comprise about 60% of its weight. The oxoborate becomes a paste at higher levels of loading with solvents or liquid ingredients.

Thus, a heretofore unaddressed need exists in the industry to address the aforementioned deficiencies and inadequacies.

SUMMARY OF THE INVENTION

The present invention provides both an effervescent system and a carrier for liquid ingredients to be used in effervescent compounds and a method for making a carrier for liquid ingredients to be used in effervescent compounds. Briefly described, the carrier is an expanded perborate salt anhydrous (EPB) which is both an effervescent material and a carrier that can be loaded with up to 1.2 times its weight with a solvent or liquid ingredient in which may be dissolved many different materials. The EPB remains a free-flowing dry powder suitable for incorporation into effervescent tablets, granules or powders.

Further, the present invention can also be viewed as providing a method for producing the EPB. The method includes the steps of heating a perborate salt monohydrate at a temperature and for an amount of time to produce the expanded perborate salt, anhydrous.

The present invention can also be viewed as providing for effervescent compounds incorporating EPB, and a method for making the effervescent compounds. In this regard, the method can be broadly summarized by the following steps: providing a solvent or liquid ingredient; providing an effervescent system, including EPB, in powder form; and mixing the solvent or liquid ingredient with the effervescent system, thereby producing a free-flowing effervescent compound. Alternative embodiments of the present invention include the further steps of dissolving ingredient(s) in a solvent or liquid ingredient and mixing the resulting solution with the effervescent system thereby producing a free-flowing effervescent compound. Further, the method may include compressing the effervescent compound and forming granules of the effervescent compound. In an alternative embodiment, the method may also include compressing the effervescent compound and forming a tablet from the effervescent compound.

Other methods, features, and advantages of the present invention will be or become apparent to one with skill in the art upon examination of the following detailed description and figure. It is intended that all such additional methods, features, and advantages be included within this description, be within the scope of the present invention, and be protected by the accompanying claims.

BRIEF DESCRIPTION OF THE DRAWINGS

The invention can be better understood with reference to the following figure. The components in the figure are not necessarily to scale, emphasis instead being placed upon clearly illustrating the principles of the present invention. Moreover, in the figure, like reference numerals designate corresponding parts throughout the several views.

DETAILED DESCRIPTION OF THE INVENTION

Figure 1:
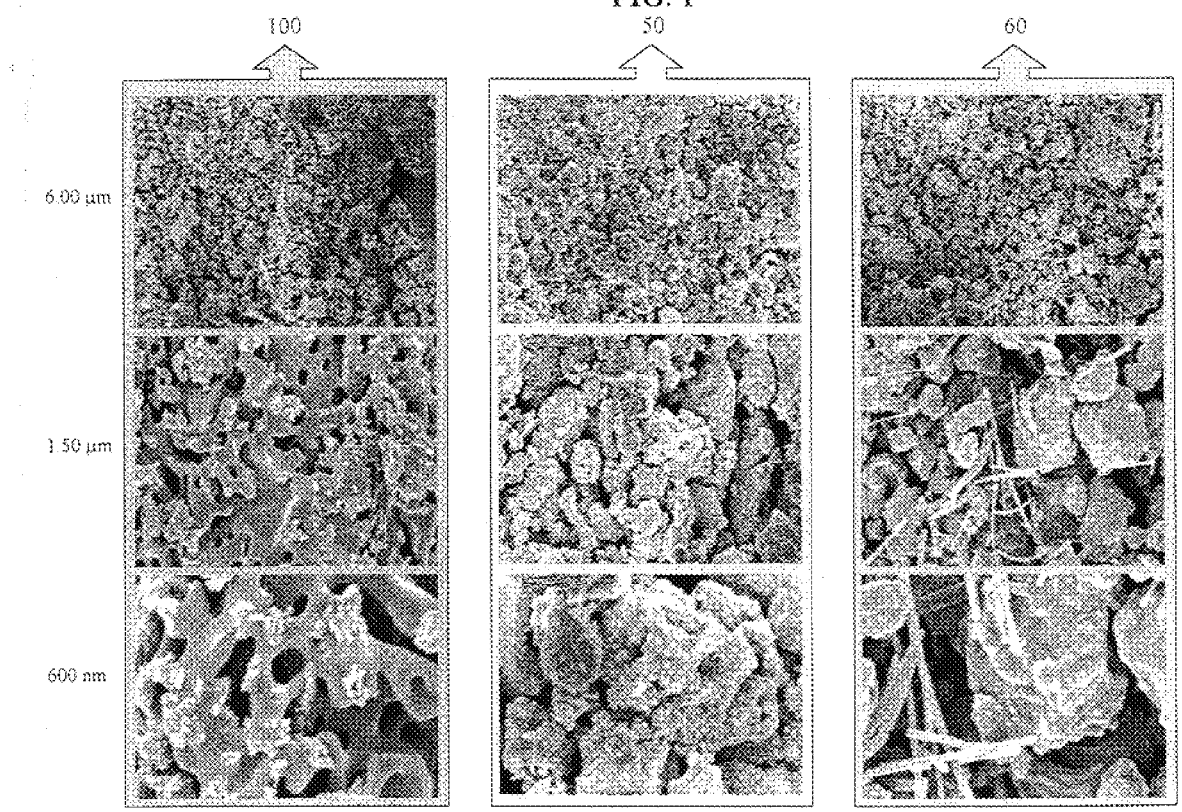
FIG. 1 is a comparison chart of photographs of Scanning Electron Micrographs (SEMs) of both conventional compounds and EPB.

The invention is able to solve the aforementioned deficiencies and inadequacies by providing and using an expanded perborate salt, anhydrous (EPB) in the production of effervescent compounds. The effervescent compounds may be in the form of tablets, granules or powders. EPB is produced by dehydration of a perborate salt, hydrate at elevated temperatures. "Perborate hydrate" in the preferred embodiment of the invention means a perborate salt, monohydrate.

EPB can adsorb significantly higher levels of liquids, up to 120% of its own weight, and remain free flowing. EPB is surprisingly very easy to tablet, and maintains its flow and tableting characteristics after adsorbing more than its own weight in liquid. Further, the amount of effervescence is sufficient to eliminate the need, if desired, for additional effervescent materials permitting effervescent tablets, granules or powders to be produced that contain up to 60% liquid ingredients.

EPB is produced by heating a perborate salt, hydrate at sufficiently high temperatures for a sufficient time to cause the loss of over 20% of its weight. Thus, EPB is produced by dehydration of a perborate, hydrate at temperatures and time sufficient so as to reduce the weight of the EPB product to less than 80% of the perborate, hydrate starting material. Generally, the temperature should be, for example, over approximately 120° C. In the preferred embodiment, the temperature of the reaction is approximately 130° C. to approximately 175° C., or higher. While there is not a set upper limit of dehydration temperature, one skilled in the art would understand that at extremely high temperatures, e.g., 1400° C., the reaction materials would decompose.

The perborate salt, hydrate is generally heated for approximately 2 minutes to approximately five hours. The reaction of perborate salt, hydrate to form EPB is time-temperature dependent, i.e., the higher the temperature (within reason), the shorter the amount of time it takes for dehydration to occur. For example, at approximately 150° C., the dehydration may occur in less than two minutes to approximately 15 minutes, while at 135° C., the dehydration may vary from approximately five minutes to approximately one hour. In the preferred embodiment of the process of dehydrating the perborate salt, hydrate to EPB, the time for dehydration is fifteen minutes or less, and possibly two to three minutes depending on temperature and other reaction conditions, such as the thickness of the layer of the perborate salt, the movement of the air, the means or method of heating the perborate salt (radiant heating, convection heating, etc.), etc.

The resulting EPB of the present invention has lower residual peroxide levels, lower bulk density, higher porosity and more surface area than commercially available sodium perborate, anhydrous (oxoborate). For example, oxoborate has a density of approximately 0.39 g/ml, or, one gram occupies a volume of approximately 2.5 ml. EPB, however, has a density of approximately 0.28 g/ml, or, one gram occupies a volume of approximately 3.5 ml.

Without wishing to be bound to any theory, it is believed that in the production of the EPB of the present invention some water vapor re-condenses on the perborate salt particles, thereby causing effervescence as oxygen is liberated. As the particles effervesce in production, voids or spaces are created in the sodium perborate salt, thereby creating an "expanded" perborate salt, anhydrous, or EPB. It seems that EPB is more of a sodium borate salt than an oxoborate. For example, if commercially available oxoborate is viewed under a microscope, it appears similar to the surface of a loosely packed snowball; however, if EPB of the present invention is viewed under the microscope, the surface of the "snowball" has many craters and voids, and appears much more irregular.

FIG. 1 depicts a comparison of scanning electron micrographs (SEM) of the EPB 100 with conventional oxoborate 50 and sodium perborate, monohydrate 60 at 6 micrometers ($\mu$m), 1.5 $\mu$m and 600 nanometers (nm). As can be clearly seen at the 1.5 $\mu$m and 600 nm magnifications, EPB 100 is significantly more porous and has more voids and interstices than either oxoborate 50 or sodium perborate, monohydrate 60.

EPB usually includes a residual amount of peroxide. In the preferred embodiment of EPB, the residual amount of peroxide, expressed as hydrogen peroxide, is less than 6% by weight of the composition, and also in the preferred embodiment is between approximately 0.5% and approximately 3% by weight of the composition. The hydrogen peroxide of oxoborate, however, is approximately 6% by weight of the oxoborate. Thus, EPB can be used in effervescent compositions in which it is not desired or necessary to have a bleaching agent. Further, because it is believed that the peroxide has already been expressed during the production of EPB, as noted above, the result is a product that is less dense and contains more voids that are able to adsorb more liquid active ingredients than conventional effervescent compositions. Depending upon the desired application, however, it is included as an embodiment of the present invention that oxoborate may be mixed with EPB described herein, in varying ratios of EPB to oxoborate. In a preferred embodiment, the EPB to oxoborate ratio is greater than one.

Table 1 below outlines the conditions under which EPB may be produced. EPB may be prepared by heating sodium perborate, monohydrate under ambient pressure. Though the invention is mainly described and explained with respect to sodium perborate, anhydrous, one skilled in the art could envision that other alkali metal perborates, anhydrous might be usable as well, such as the alkali metals of lithium (Li), potassium (K), rubidium (Rb), and cesium (Cs). In applications where it is not necessary for EPB to be water soluble, alkaline earth metal perborates may also be used to produce EPB, including beryllium (Be), magnesium (Mg), calcium (Ca), strontium (Sr), and barium (Ba).

TABLE 1

Conditions for Production of EPB

| Sample # | Temperature | Time | Weight Loss | $H_2O_2$ | Density (g/ml) |
|---|---|---|---|---|---|
| 1 | 135° | 0.25 hr | 16% | 2.7% | |
| 2 | | 0.5 hr | 20.5% | 1.7% | |
| 3 | | 1 hr | 21.5% | 0.9% | |
| 4 | | 2 hr | 26.3% | 0.8% | |
| 5 | | 5 hr | 26.9% | 0.5% | 0.28 |
| 6 | 170° | 0.25 hr | 26.9% | 2.7% | |
| 7 | | 0.5 hr | 26.9% | 2.3% | |
| 8 | | 1 hr | 26.9% | 1.5% | |
| 9 | | 2 hr | 27% | 0.8% | |
| 10 | | 5 hr | 27% | 0.8% | 0.27 |

Tableting characteristics of the above samples were compared to commercially available sodium oxoborate. Samples were loaded with 0%, 50% and 100% of their weight with 2-butoxyethanol. The liquid loaded samples were then mixed with 2% sodium benzoate as a lubricant, and two gram tablets were pressed at 0.6 tons using a 19.5 mm punch and die. Tables 2 and 3 below compares the results of tablets made of conventional oxoborate with tablets made with expanded sodium perborate, anhydrous (ESPB) of the present invention.

TABLE 2

Hardness Comparison of Oxoborate with ESPB at Various Loading Levels

| Sample | Loading | Tablet Hardness (relative factors) |
|---|---|---|
| Oxoborate | 0% | 7 |
| | 50% | 3 |
| | 100% | Liquid |
| EPB - Sample 2 | 0% | >40 |
| | 50% | 18 |
| | 100% | 5 |
| EPB - Sample 3 | 0% | >40 |
| | 50% | 20 |
| | 100% | 5 |
| EPB - Sample 4 | 0% | >40 |
| | 50% | 20 |
| | 100% | 6 |
| EPB - Sample 7 | 0% | >40 |
| | 50% | 21 |
| | 100% | 8 |
| EPB - Sample 8 | 0% | >40 |
| | 50% | 23 |
| | 100% | 9 |
| EPB - Sample 9 | 0% | >40 |
| | 50% | 21 |
| | 100% | 10 |

TABLE 3

Comparison of Characteristics of Conventional Sodium Perborate, Monohydrate; Oxoborate; and ESPB

| | Conventional Sodium Perborate, Monohydrate | Oxoborate | ESPB |
|---|---|---|---|
| Scanning Electron Microscope (See FIG. 1) | Crystalline, porous | Amorphous, non-porous | Amorphous, many open pores |
| Bulk Density | 0.55–0.60 kg/l | 0.3–0.4 kg/l | 0.24–0.28 kg/l |
| $H_2O_2$ | 32–36% | 4–6% | 0.5–3% |
| Liquid Loading (gram 2-butoxyethanol/g carrier) | 0.3:1 | 0.7:1 | 1.2:1 |
| Tablet Hardness | | | |
| unloaded carrier | 15 | 7 | 25 |
| loaded carrier 0.3:1 | 2 | 4 | 12 |
| loaded carrier 0.7:1 | na | 2 | 8 |
| loaded carrier 1.0:1 | na | na | 4 |
| loaded carrier 1.2:1 | na | na | 2 |
| $O_2$ gas produced with water | na | 13% | 3–5% |
| pH (1% solution) (approximate range) | 10.2–10.5 | 10–10.4 | 10.6–10.8 |

It is apparent from the above data that the ESPB of the present invention provides substantially improved loading and tableting characteristics over conventional oxoborate. By using expanded sodium perborate EPB as the carrier to hold all liquid ingredients for the tablets, liquid surfactants may be loaded at high levels into the effervescent products. Solvents, both volatile, e.g., alcohols or ethers; and non-volatile, e.g., glycerine or propylene glycol, can be loaded at high levels and used in the effervescent products. Further, oils and fragrances may be loaded at high levels and used in the effervescent products as well. In the effervescent products of the present invention, solvents can be used to dissolve various active ingredients such as surfactants or quaternary ammonium salts (quats), and loaded onto the carrier, i.e., EPB, for use in the effervescent tablets. It should be noted that this dissolution increases the solubility rate of hydrophobic ingredients. Up to a 1.2:1 loading ratio of liquids to EPB can be used, and the resulting free-flowing powder may be used in effervescent tablets or granules.

Further, the pH of compositions made with EPB of the present invention may be alkaline, as evidenced by the alkalinity demonstrated by EPB in Table 3 above. Thus, EPB may be used as an alkalinity builder in certain compositions, rendering the compositions pH greater than approximately nine. This may enhance detergency of a composition including EPB as an ingredient.

The solvents used in the present invention can be used to dissolve many active ingredients which, in addition to being able to increase the amount of active ingredients used in effervescent compounds, also results in an improved solubility rate for the effervescent compound when added to an aqueous or other type of solution. In various embodiments of the present invention, many different solvents may be used, including both hydrophobic and hydrophilic solvents. In the preferred embodiment, the solvent is sufficiently hydrophilic to be used in aqueous products, but does not initiate an effervescent reaction with the effervescent ingredients of the effervescent compound i.e., has low solubility in the effervescent ingredients. Preferably, the solvent itself can also be used as an active ingredient in the effervescent compound. In one embodiment of the present invention, the solvent includes glycol ether. In the preferred embodiment, the solvent comprises, for example, but is not limited to, 2-butoxyethanol. Solvents of this type used in the present invention do not adversely affect either the physical or chemical stability of the effervescent compound, and may also provide added cleaning performance.

The effervescent compound including the solvent described above may be formed into a tablet. For the purposes of this document, "tablet" means both tablets and the granular form of effervescent products, and "granular" means generally uniform-sized compressed mixtures. Tablets produced using EPB of the present invention are shelf stable and have good physical properties. For example, but not limited to these physical characteristics, the tablets may be hard; non-friable; of minimum size, both in weight and dimension for the desired application; and have an increased dissolution rate over tablets not made with the EPB of the present invention.

The effervescent system of the present invention may include, for example, but is not limited to, EPB, or EPB plus oxoborate, or EPB plus a mixture of an acid and one or more of sodium bicarbonate, sodium carbonate, potassium carbonate and potassium bicarbonate or EPB plus oxoborate plus a mixture of an acid and one or more of sodium bicarbonate, sodium carbonate, potassium carbonate and potassium bicarbonate. Typically, the effervescent system is in a powdered form. If EPB is used alone as the effervescent system, the solvent or liquid ingredients may be present in the effervescent compound of the present invention in an amount up to approximately 55% by weight of the composition. If, however, a carbonate/acid system is used as the major effervescent ingredient, the solvent or liquid ingredients may be limited to approximately 35% by weight of the effervescent compound. If the solvent is used alone with the effervescent system, and no other ingredients are added, the solvent itself may act as a cleaning ingredient, including, for example, but not limited to, a "degreaser," which is a compound that will render oils miscible with water.

Many other ingredients may also be added to the solvent and included in the effervescent compound. These additional ingredients that may be added to a solvent and then loaded onto the EPB of the present invention include, but are not limited to, any one, all, or any combination of the following: surfactants, bleaching compositions, optical brighteners, anti-redeposition agents, chelating or sequestering agents, binders, lubricants, colors, pesticides, anti-corrosives and/or fragrances. These ingredients may be used in any combination and percentage ratio, depending on the application sought for the effervescent compound of the present invention. If EPB is used alone as the effervescent system, these combined ingredients may be present in an amount up to 50% by weight of the effervescent compound. If, however, the carbonate/acid effervescent system is used as the major effervescent ingredient, these ingredients may be limited to approximately 35% by weight of the effervescent compound.

Exemplary surfactants that may be added to the effervescent compound include, but are not limited to: synthetic anionic surfactants, which are generally water-soluble alkali metal salts of organic sulfates and sulfonates; non-ionic surfactants, which are generally the reaction products of alkylene oxide with alkyl phenol, or primary or secondary alcohols, or are amine oxides, phosphine oxides or dialkyl sulphoxides; amphoteric; or zwitterionic surfactants and/or soaps. Examples of the bleaching composition that may be used include, but are not limited to, chlorinated isocyanurates, perborate hydrates, persulfates or percarbonates. Examples of anti-redeposition agents include, but are not limited to, acrylates and cellulose derivatives. The binder used in the effervescent of the present invention may include, for example, but are not limited to any one, all, or any combination of the following: starch and starch derivatives, cellulose and cellulose derivatives, carbohydrate gums, sugars, resins, proteins and inorganic salts. Examples of lubricants that may be used in the effervescent compound of the present invention include, but are not limited to any one, all, or any combination chosen from the following: sodium benzoate, sodium stearate, magnesium stearate, aluminum stearate, stearic acid, mineral oil and polyethylene glycol.

There are several examples of effervescent products that may be made with the EPB, for example including, but not limited to, a carpet cleaner, a dish detergent, a glass cleaner, a laundry detergent, a sanitizer and/or a hard surface cleaner/disinfectant. Other effervescent products that may be made with the carrier of the present invention are not limited to cleaners, but also include an adsorbent, a dry lubricant, a dry solvent, a fertilizer, a fragrance dispenser, a fungicide, an insecticide, an herbicide, a packing material, a rust inhibitor, a fabric softener, a wrinkle releaser agent, a furniture polish, a preservative, a deodorizer, a car detergent, a car wax, and various shampoos, soaps, bath salts, bath fizzes, and bubble baths.

Applications for these various types of effervescent products could be envisioned by one skilled in the art. EPB need not be used solely for its effervescent characteristics. For example, but not limited to the applications for making an effervescent, EPB could be also used in the industrial and institutional setting, in which a solvent can be used as a cleaner, followed by adsorbing the solvent with EPB and perhaps recovering the solvent. Further, hazardous materials spills could be contained and adsorbed in dry form and potentially recovered by using an effervescent product made with EPB. Additionally, EPB could be used in an effervescent product that could pick up kitchen fats or oils by adsorbing them to produce a dry powder, which could then be swept up. EPB could be used in an effervescent product so that the product could be used as a lubricant in dry form that would be released upon exposure to humidity. Additionally, EPB could be used in dry solvent products, for example, but not limited to, a dry single dose charcoal lighter.

Similarly, EPB may be incorporated into products that could be used in the home and garden, or an agricultural setting. For example, EPB could be used in a fertilizer product, e.g., a dry pre-measured dose for a garden sprayer or hand sprayer. Further, EPB could be used in a dry application as a fungicide, e.g. crop dusting, or a dry pre-measured dose for a garden sprayer or hand sprayer. Similarly, EPB could be used in an insecticide as a dry application, e.g., crop dusting, or a dry pre-measured dose for a garden sprayer or hand sprayer. Further, EPB may be used as an insecticide in roach and ant dry insecticide applications, as well as flea and tick shampoos for domesticated animals or agricultural livestock. Similarly, EPB could be used as herbicide as a dry application, e.g., a crop dusting, or dry pre-measured dose garden sprayer or hand sprayer.

Additionally, EPB may be use as a packing material for volatile liquids, or hazardous materials. Further, EPB may be used as a rust inhibitor, for example but not limited to dental equipment and utensil applications, such as morpholine, imidazoline, or benzotriazole. EPB may also be used in application as a sanitizer, for example but not limited to, the dental industry in which the product could hold in dry form quaternary ammonium salts (quats) or phenols with alcohol. This could provide an alternative hospital grade disinfectant or sanitizer in tablet form.

Listed herein are exemplary compositions of some sample cleaners that may be produced using EPB. The effervescent carpet cleaner that may be made using EPB can include up to 18% by weight of the composition of solvent, which had not previously been accomplished in effervescent cleaners. Further, the carpet cleaner using EPB can include surfactant(s) up to approximately 15% by weight of the composition, which is three times the usual concentration of surfactant that has been used heretofore in effervescent cleaners. Fragrance may be included up to approximately 3% by weight of the composition. Further, the carpet cleaner may include liquid ingredients up to approximately 36% by weight of the effervescent cleaner, which is five to ten times the amount that was previously possible for the liquid concentration in conventional effervescent cleaners. Further, the carpet cleaner tablet made from EPB of the present invention has a dissolution time of less than five minutes at 40° C. when dissolved for use as a cleaning aid.

Another example of a cleaner that may be produced using EPB is a glass cleaner. The glass cleaner of the present invention may be made in, for example, but not limited to, tablet form. The glass cleaner may incorporate up to 30% solvent by weight of the composition, which had not previously been accomplished in conventional effervescent products. Further, the glass cleaner may include up to approximately 5% by weight surfactant(s), and liquid ingredients up to approximately 35% by weight of the composition. Further, the glass cleaner also has a dissolution time of less than approximately five minutes at approximately 40° C. when dissolved for use as a cleaning aid.

Another example of a possible cleaner that may be produced using EPB is a laundry detergent. This laundry detergent of the present invention may include liquid surfactant(s) in an amount up to approximately 24% by weight of the composition, an amount that had not previously been accomplished in effervescent cleaners. The laundry detergent may also include up to approximately 5% fragrance, which is two to five times the amount that has been used in typical effervescent formulas. The laundry detergent has a dissolution time of less than five minutes at 20° C. when dissolved for use as a cleaning aid.

Another example of a possible cleaner that may be produced using EPB is a hard surface cleaner/disinfectant. The hard surface cleaner of the present invention may include solvent in an amount up to approximately 24% by weight of the composition, an amount that had not previously been accomplished in conventional hard surface cleaners. The hard surface cleaner may also include up to approximately 15% quats, which is five times the amount that has been used in conventional effervescent products tablets. This amount of loading is important to rendering the tablet more effective, or for making effective smaller tablets. The hard surface cleaner may include surfactant(s) in an amount up to approximately 5% by weight of the composition, and total active ingredient(s) in an amount of approximately 39% by weight of the composition. The hard surface cleaner also has a dissolution time of less than approximately five minutes at approximately 40° C. when dissolved for use as a cleaning aid.

Also included within the scope of the invention is a method for making an effervescent compound that includes the steps of providing a solvent, providing an effervescent system in powder form that includes EPB, and mixing the solvent with the effervescent system, thereby producing a free-flowing effervescent compound. The method may also include the steps of compressing the compound and forming either granules or a tablet of the effervescent compound. The solvent used in the step of providing a solvent may be either hydrophobic or hydrophilic. In the preferred embodiment, however, the solvent is hydrophilic and has low solubility with effervescent ingredients. "Low solubility" for the purposes of this document means that the solvent has insignificant solubility with effervescent ingredients. This prevents reaction and effervescence of the product before use. The solvent may be, for example, but is not limited to, any one or any combination of the following: glycols, alcohols and glycol ethers, e.g., 2-butoxyethanol.

The effervescent system that is used in the step of providing an effervescent system in powder form may be, for example, but is not limited to EPB or EPB plus oxoborate, or EPB plus a mixture of an acid and one or more of sodium bicarbonate, sodium carbonate, potassium carbonate and potassium bicarbonate or EPB plus oxoborate plus a mixture of an acid and one or more of sodium bicarbonate, sodium carbonate, potassium carbonate and potassium bicarbonate. The method may further include the steps of providing other ingredients in a powder form that are to be mixed with a solvent and the effervescent system, thereby producing the effervescent compound. These ingredients include, but are not limited to, any one, all, or any combination of the following in any percentage ratio: surfactants, bleaching compositions, optical brighteners, anti-redeposition agents, binders, lubricants, colors, corrosion inhibitors, disinfectants, pesticides, fertilizers and/or fragrances. If necessary, these ingredients may be mixed with or dissolved in a solvent or mixture of solvents, and, if necessary, distilled to remove any water or low boiling-point alcohol before being loaded onto the EPB. The resulting liquid can then be used in the effervescent compound. It should be noted that the resulting effervescent compound including the EPB is stable and has good tableting and dissolution characteristics.

It should be emphasized that the above-described embodiments of the present invention, particularly, any "preferred" embodiments, are merely possible examples of implementations, and are merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A composition for use in production of effervescent compounds comprising:
   an expanded perborate salt, anhydrous, wherein the expanded perborate salt, anhydrous is able to load t-butoxyethanol in a ratio of t-butoxyethanol to expanded perborate salt, anhydrous up to 1.2:1.

2. The composition of claim 1, wherein the expanded perborate salt anhydrous, adsorbs a high percentage of liquid active ingredients.

3. The composition of claim 1, wherein the expanded perborate salt, anhydrous adsorbs liquid active ingredients that comprise approximately 50 percent by weight of the composition.

4. The composition of claim 1, wherein the expanded perborate salt anhydrous is an expanded alkali metal perborate, anhydrous.

5. The composition of claim 4, wherein the expanded alkali metal perborate anhydrous is expanded sodium perborate, anhydrous.

6. The composition of claim 1, wherein the expanded perborate salt, anhydrous has a residual amount of a peroxide.

7. The composition of claim 6, wherein the residual amount of the peroxide is between approximately 0.5% and approximately 3% expressed as hydrogen peroxide.

8. The composition of claim 1, wherein the composition further comprises oxoborate.

9. An effervescent composition comprising:
   a solvent that has low solubility with effervescent ingredients, and comprises up to approximately 55% by weight of the compound; and
   an effervescent system that comprises expanded perborate salt, anhydrous, wherein the expanded perborate salt, anhydrous is able to load t-butoxyethanol in a ratio of t-butoxyethanol to expanded perborate salt, anhydrous up to 1.2:1.

10. The composition of claim 1, wherein the composition provides sufficient alkalinity to enhance detergency.

11. A method of cleaning by contacting a surface to be cleaned with a solution obtained by dissolving in water the effervescent composition of claim 1.

12. A method of adsorbing materials by contacting the materials with the effervescent composition of claim 1.

13. The method of claim 12, wherein the adsorbed materials are hazardous.

14. A method of fertilizing a plant by contacting the plant with a solution obtained by dissolving in water the effervescent composition of claim 1.

15. A method of destroying a plant by contacting the plant with a solution obtained by dissolving in water the effervescent composition of claim 1.

16. A method of destroying an insect or arachnid by contacting the insect or arachnid with a solution obtained by dissolving in water the effervescent composition of claim 1.

17. A method of inhibiting corrosion by contacting a metal that corrodes with a solution obtained by dissolving in water the effervescent composition of claim 1.

18. A method of sanitizing or disinfecting by contacting a surface to be sanitized or disinfected with a solution obtained by dissolving in water the effervescent composition of claim 1.

19. A method of deodorizing by contacting a surface to be deodorized with a solution obtained by dissolving in water the effervescent composition of claim 1.

20. An expanded perborate salt anhydrous compound, prepared by a process comprising the steps of:
   providing a perborate salt, monohydrate; and
   dehydrating the perborate salt, monohydrate under ambient pressure, wherein the expanded perborate salt, anyhydrous is able to load t-butoxyethanol in a ratio of t-butoxyethanol to expanded perborate salt, anhydrous up to 1.2:1.

21. The product by the process of claim 20, wherein the step of dehydrating the perborate salt, monohydrate comprises the step of heating the perborate salt, monohydrate.

22. The product by the process of claim 21, wherein the step of heating the perborate salt, monohydrate comprises the step of placing the perborate salt, monohydrate in an oven.

23. The product by the process of claim 22, wherein the step of placing the perborate salt, monohydrate in an oven comprises placing the perborate salt, monohydrate in a dry oven.

24. The product by the process of claim 20, wherein the step of heating the perborate salt, monohydrate comprises heating the perborate salt, monohydrate at a temperature in the range between approximately 130° C. and approximately 175° C.

25. The product by the process of claim 20, wherein the step of heating the perborate salt, monohydrate comprises heating the perborate salt, monohydrate for approximately fifteen minutes to approximately five hours.

26. The product by the process of claim 20, wherein the step of heating the perborate salt, monohydrate comprises heating the perborate salt, monohydrate for less than fifteen minutes.

27. The product by the process of claim 20, wherein the expanded perborate salt, anhydrous is expanded sodium perborate, anhydrous.

28. The product by the process of claim 27, further including oxoborate.

29. The product by the process of claim 20, wherein the step of dehydrating the perborate salt, monohydrate comprises the step of dehydrating the perborate salt, monohydrate at temperatures and time sufficient to reduce the weight of the expanded perborate salt, anhydrous compound to less than 80% of the perborate salt, monohydrate.

30. A method for making an effervescent composition comprising the steps of:
   providing a solvent that has low solubility with effervescent ingredients, in an amount up to approximately 55% by weight of the compound;
   providing an effervescent system in powder form that includes expanded perborate salt, anhydrous, wherein the expanded perborate salt, anhydrous is produced by dehydration of a perborate, monohydrate at a temperature greater than 120° C.; and
   mixing the solvent with the effervescent system, thereby producing a free-flowing effervescent compound.

31. The method of claim 30, further comprising the steps of:
   compressing the effervescent composition; and
   forming granules of the effervescent composition.

32. The method of claim 30, further comprising the steps of:
   compressing the effervescent composition; and
   forming a tablet from the effervescent composition.

33. The method of claim 30, wherein the step of providing an effervescent system that includes expanded perborate salt, anhydrous comprises providing an effervescent system in powder form that further includes an acid and one or more of sodium bicarbonate; sodium carbonate; potassium bicarbonate and potassium carbonate.

34. The method of claim 30, wherein the step of providing an effervescent system that includes expanded perborate salt, anhydrous comprises providing an effervescent system in powder form that further includes oxoborate.

35. The method of claim 30, wherein the step of providing an effervescent system that includes expanded perborate salt, anhydrous comprises providing an effervescent system in powder form that further includes oxoborate and an acid and one or more of sodium bicarbonate; sodium carbonate; potassium bicarbonate and potassium carbonate.

36. The method of claim 30, wherein the step of providing an effervescent system that includes expanded perborate salt, anhydrous comprises providing an effervescent system that includes expanded alkali metal perborate, anhydrous.

37. The method of claim 36, wherein the step of providing an effervescent system that includes expanded alkali metal perborate, anhydrous includes providing expanded sodium perborate, anhydrous.

38. The method of claim 30, wherein the step of providing an effervescent system that includes expanded perborate salt, anhydrous comprises providing an effervescent system that includes an expanded perborate salt, anhydrous that adsorbs liquid active ingredients that comprise approximately 50% by weight of the composition.

39. The method of claim 30, wherein the step of providing an effervescent system that includes expanded perborate salt, anhydrous comprises providing an effervescent system that includes a mixture of an expanded perborate salt, anhydrous and oxoborate.

40. The method of claim 30, wherein the effervescent composition made is chosen from: an adsorbent, a dry lubricant, a dry solvent, a fertilizer, a fragrance dispenser, a fungicide, an insecticide, an herbicide, a packing material, a rust inhibitor, and a sanitizer.

41. The composition of claim 9, wherein the expanded perborate salt anhydrous, adsorbs a high percentage of liquid active ingredients.

42. The composition of claim 9, wherein the expanded perborate salt, anhydrous adsorbs liquid active ingredients that comprise approximately 50 percent by weight of the composition.

43. The composition of claim 9, wherein the expanded perborate salt, anhydrous is an expanded alkali metal perborate, anhydrous.

44. The composition of claim 43, wherein the expanded alkali earth metal perborate, anhydrous is expanded sodium perborate, anhydrous.

45. The composition of claim 9, wherein the expanded perborate salt, anhydrous has a residual amount of peroxide.

46. The composition of claim 45, wherein the residual amount of peroxide is between approximately 0.5% and approximately 3% expressed as hydrogen peroxide.

47. The composition of claim 9, wherein the effervescent system further comprises oxoborate.

48. The composition of claim 9, in which the effervescent system is used to produce at least one of the following: an adsorbent, a dry lubricant, a dry solvent, a fertilizer, a fragrance dispenser, a fungicide, an insecticide, an herbicide, a packing material, a rust inhibitor, a sanitizer, a fabric softener, a wrinkle releaser agent, a furniture polish, a preservative, a deodorizer, a car detergent, a car wax, shampoos, soaps, bath salts, bath fizzes and bubble baths.

* * * * *